(12) United States Patent
Mizushima et al.

(10) Patent No.: US 8,546,329 B2
(45) Date of Patent: Oct. 1, 2013

(54) ERYTHROPOIETIN SOLUTION PREPARATION

(75) Inventors: Hidefumi Mizushima, Tokyo (JP); Takayuki Yoshimori, Tokyo (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 605 days.

(21) Appl. No.: 12/293,493

(22) PCT Filed: Mar. 22, 2007

(86) PCT No.: PCT/JP2007/055860
§ 371 (c)(1),
(2), (4) Date: Sep. 18, 2008

(87) PCT Pub. No.: WO2007/108505
PCT Pub. Date: Sep. 27, 2007

(65) Prior Publication Data
US 2010/0234276 A1    Sep. 16, 2010

(30) Foreign Application Priority Data
Mar. 22, 2006    (JP) .................................. 2006-078609

(51) Int. Cl.
*C07K 14/505* (2006.01)
(52) U.S. Cl.
USPC ............................................ 514/7.7; 514/7.9
(58) Field of Classification Search
USPC .................................................. 514/7.7, 7.9
See application file for complete search history.

(56) References Cited

U.S. PATENT DOCUMENTS

| | | | |
|---|---|---|---|
| 4,677,195 A | 6/1987 | Hewick et al. | |
| 4,879,272 A | 11/1989 | Shimoda et al. | |
| 6,120,761 A | 9/2000 | Yamazaki et al. | |
| 6,277,367 B1 | 8/2001 | Yamazaki et al. | |
| 6,627,187 B2 | 9/2003 | Yamazaki et al. | |
| 6,908,610 B1 | 6/2005 | Sato | |
| 7,011,825 B2 | 3/2006 | Yamazaki et al. | |
| 7,169,754 B2 * | 1/2007 | Papadimitriou | 514/7.7 |
| 7,202,208 B2 | 4/2007 | Papadimitriou | |
| 7,534,870 B2 * | 5/2009 | Vukmirovic et al. | 530/388.23 |
| 7,790,679 B2 * | 9/2010 | Li et al. | 514/7.7 |
| 2001/0055582 A1 | 12/2001 | Yamazaki et al. | |
| 2004/0038878 A1 | 2/2004 | Tanikawa et al. | |
| 2004/0087507 A1 | 5/2004 | Yamazaki et al. | |
| 2004/0110679 A1 | 6/2004 | Lehmann et al. | |
| 2005/0202091 A1 | 9/2005 | Vukmirovic et al. | |
| 2005/0238720 A1 * | 10/2005 | Vukmirovic et al. | 424/486 |
| 2006/0159653 A1 | 7/2006 | Saito et al. | |
| 2007/0293419 A1 | 12/2007 | Kwon et al. | |
| 2009/0264629 A1 | 10/2009 | Saito et al. | |

FOREIGN PATENT DOCUMENTS

| | | |
|---|---|---|
| EP | 1598074 A1 | 11/2005 |
| WO | 85-02610 | 6/1985 |
| WO | 86-03520 | 6/1986 |
| WO | 91-05867 | 5/1991 |
| WO | 95-05465 | 2/1995 |
| WO | 97-02811 | 1/1997 |
| WO | 02/11753 | 2/2002 |
| WO | WO-02/092147 A2 | 11/2002 |
| WO | WO-2004/002534 A1 | 1/2004 |
| WO | 2004-075913 | 9/2004 |
| WO | WO-2004/108152 A1 | 12/2004 |

OTHER PUBLICATIONS

Abstract of JP 2001-64300 (Mar. 2001).*
Wilfried Kramer et al., "The gapped duplex DNA approach to oligonucleotide-directed mutation construction", Nucleic Acids Research, vol. 12; No. 24, p. 9441-9456, 1984.
Douglass, S.A. et al, Methods and instrumentation for fluorescence quantitation of proteins and DNA's in electrophoresis gels at the 1 ng level, Developments in Biochemistry, 1978, vol. 2(Electrophoresis), p. 155-65.
Suzuki, Y. et al, Design and synthesis of intramolecular charge transfer-based fluorescent reagents for the highly-sensitive detection of proteins, J. Am. Chem. Soc., 2005, vol. 127, No. 50, p. 17799-802.
Wheeler, J.X. wt al, Mass spectrometric analysis of maleimide CyDye labelled model peptides, Rapid Commun. Mass Spectrom., 2003, vol. 17, No. 22. p. 2563-6.
Kenneth Jacobs et al., "Isolation and characterization of genomic and cDNA clones of human erythropoietin", Nature, 313, 806-810 (1985).
Gotoh, T. et al., "An oligodeoxyribonucleotide-directed dual amber method for site-directed mutagenesis", Gene, 152 (1995) 271-275.
Kunkel et al., "Rapid and efficient site-specific mutagenesis without phenotypic selection", Proc. Natl. Acad. Sci USA; vol. 82, pp. 488-492.(1995).
Mark et al., "Site-specific mutagenesis of the human fibroblast interferon gene", Proc. Natl. Acad. Sci. USA; vol. 81, pp. 5662-5666. 1984.
Zoller and Smith et al., "Oligonucleotide-directed mutagenesis using M13-deriver vectors: an efficient and general procedure for the production of point mutations in any fragment of DNA", Nucleic Acids Search vol. 10, 1982.
Wang et al., Site-Specific Mutagenesis of the human interleukin-2 Gene: structure-function analysis of the cysteine residues, Science, 224: pp. 1431-1433.(1984).
Dalbadie-McFarland et al., "Oligonucleotide-directed mutagenesis as a general and powerful method for studies of protein function", Proc Natl Acad Sci USA, vol. 79, pp. 6409-6413: 1982.
Kramer and Fritz et al., "Oligonucleotide-Directed construction of mutations via gapped duplex DNA", Methods in Enzymology vol. 154, p. 350-367, 1987.
Zolller et al., Oligonucleotide-Directed Mutagenesis of DNA Fragments Cloned into M13 Vectors, Methods in Enzymology vol. 100, Recombinant DNA (1983).

\* cited by examiner

*Primary Examiner* — David Lukton
(74) *Attorney, Agent, or Firm* — McDermott Will & Emery LLP (57) ABSTRACT

The present invention relates to an erythropoietin-containing solution preparation containing a poloxamer and having a pH of 6.5 to 7.5. The present invention also relates to a method for quantifying a protein in a trace amount, the method including the following steps: binding a protein sample to a high-intensity fluorescent dye; separating a desired analyte from the obtained sample by an appropriate separation means; and quantifying the desired analyte and converting the amount of the analyte into the amount of the protein.

11 Claims, 7 Drawing Sheets

Cy5 : Low Range

Cy5 : Full Range

Figure 6

Alexa 647 : Full Range

Alexa 647 : Low Range

Figure 7

HiLyte Fluor 647 : Full Range

HiLyte Fluor 647 : Low Range

ERYTHROPOIETIN SOLUTION PREPARATION

CROSS REFERENCE TO PRIOR RELATED APPLICATIONS

This application is a United States national phase application under 35 U.S.C. §371 of International Patent Application No. PCT/JP2007/055860, filed on Mar. 22, 2007, and claims the benefit of Japanese Patent Application No. 2006-078609, filed on Mar. 22, 2006, both of which are incorporated by reference herein. The International Application was published in Japanese on Sep. 27, 2007, as International Publication No. WO 2007/108505 A1 under PCT Article 21(2).

FIELD OF THE INVENTION

The present invention relates to an erythropoietin-containing solution preparation. Particularly, the present invention relates to an erythropoietin-containing solution preparation which has little loss of an active ingredient even after long-term storage, significantly inhibits production of a dimer or decomposition product, and can alleviate pain in use.

The present invention further relates to a method for quantifying a protein in a trace amount, which is useful both for the quantification of the erythropoietin-containing solution preparation and for a purity test.

BACKGROUND OF THE INVENTION

Erythropoietin (hereinafter, also referred to as EPO), an acidic glycoprotein hormone that promotes the differentiation or growth of erythroid progenitor cells, is produced in large amounts as recombinant human EPO by a genetic engineering method. The present applicant has successfully developed a preparation of this purified EPO and introduced, to the market, a product thereof in the form of a freeze-dried or solution preparation as a renal anemia-improving agent or the like.

An EPO solution preparation containing, as a stabilizer, an amino acid selected from leucine, tryptophan, serine, glutamic acid, arginine, histidine, and lysine, and salts thereof, has been proposed as a formulation for introducing a stable EPO solution preparation to the market (Japanese laid-open Patent Publication No. 2000-247903).

The stability of a physiologically active protein solution largely depends on the pH of the solution, and this protein solution is relatively stable at an acidic pH. EPO has been known to be stable at an acidic pH around 6.0. An EPO solution preparation stable even after long-term storage that is currently on the market is a product having a weakly acidic pH of 6.0, which slightly deviates from the in-vivo pH. However, the subcutaneous injection of such a weakly acidic solution preparation is expected to involve pain. The development of an EPO solution preparation that is further improved in usability and is stable even after long-term storage has been demanded.

The addition of saccharides such as mannitol has been proposed as a method for alleviating pain involved in the administration of a preparation for injection (WO 02/11753).

Alternatively, an antibody preparation containing a poloxamer as a surfactant has been reported (WO 2004/075913). However, this document has made no description of the stability of a solution preparation containing EPO or pain involved in injection.

An object of the present invention is to provide an EPO solution preparation which alleviates pain involved in injection and is stable even after long-term storage. A further object of the present invention is to provide a method for quantifying a protein in a trace amount, which is useful both for the quantification of the erythropoietin-containing solution preparation and for a purity test.

SUMMARY OF THE INVENTION

The present inventors have conducted diligent studies for attaining the object and have consequently completed the present invention by finding out that the use of a poloxamer as a surfactant achieves an erythropoietin-containing solution preparation which is stable at the long term and alleviates pain involved in injection even at a pH of approximately 7.0.

Among other features, the present invention provides an erythropoietin-containing solution preparation containing a poloxamer and having a pH of 6.5 to 7.5.

The present invention also provides the preparation according to the description above, wherein the poloxamer is poloxamer 188.

The present invention further provides the preparation according to the description above, further containing an amino acid or a salt thereof as a stabilizer.

The present invention further provides the preparation according to the description immediately above, wherein the amino acid is histidine, arginine, or a salt thereof.

The present invention further provides the preparation according to any of the descriptions above, wherein the pH is 6.8 to 7.2.

The present invention further provides an erythropoietin-containing solution preparation containing a poloxamer and L-histidine as a stabilizer and having a pH of 6.8 to 7.2.

The present invention further provides the preparation according to any of the descriptions above, wherein the preparation is free of a protein as a stabilizer.

The present invention further provides the preparation according to any of the descriptions above, wherein the preparation is free of sugars as a stabilizer.

The present invention further provides a method for inhibiting the production of an erythropoietin dimer after long-term storage of an erythropoietin-containing solution preparation, the method including the step of adding a poloxamer.

The present invention further provides a method for quantifying a protein in a trace amount, the method including the following steps:

binding a protein sample to a high-intensity fluorescent dye;

separating a desired analyte from the obtained sample by an appropriate separation means; and quantifying the desired analyte and converting the amount of the analyte into the amount of the protein.

The present invention further provides the quantifying method according to the description immediately above, wherein the high-intensity fluorescent dye is a Cyanine Dye-based dye.

The present invention further provides the quantifying method according to the description immediately above, wherein the high-intensity fluorescent dye is Cy3.

The present invention further provides the quantifying method according to any of the descriptions above, wherein the separation means is electrophoresis or high-performance liquid chromatography (HPLC).

The present invention further provides the quantifying method according to any of the descriptions above, wherein the protein in a trace amount is erythropoietin.

DETAILED DESCRIPTION OF THE INVENTION

Any EPO can be used as EPO used in a preparation of the present invention. Preferably, highly purified EPO is used. More specifically, those having substantially the same biological activity as that of mammal EPO, particularly human EPO, are used.

The EPO used in the present invention may be produced by any method. For example, natural human EPO obtained by purification from a human-derived extract (e.g., Japanese Patent examined Publication No. 1-38800) or human EPO that is produced in E. coli, yeast, Chinese hamster ovary cells (CHO cells), C127 cells, COS cells, myeloma cells, BHK cells, insect cells, and the like by a genetic engineering approach and extracted by a variety of methods, followed by separation and purification, can be used. The EPO used in the present invention is preferably EPO produced by a genetic engineering approach, more preferably EPO produced using mammal cells (particularly, CHO cells) (e.g., Japanese Patent Examined Publication No. 1-44317; and Kenneth Jacobs et al., Nature, 313, 806-810 (1985)).

The EPO obtained by a genetic recombination method may be, for example, those having the same amino acid sequence as that of naturally existing EPO or those having the amino acid sequence with the deletion, substitution, addition, or the like of one or several amino acids therein and having biological activity similar to the naturally existing EPO. The deletion, substitution, addition, or the like of amino acids can be performed by a method known by one skilled in the art. For example, one skilled in the art can prepare a polypeptide functionally equivalent to EPO by introducing an appropriate mutation in EPO amino acids using a site-specific mutagenesis method (Gotoh, T. et al. (1995) Gene 152, 271-275; Zoller, M. J. and Smith, M. (1983) Methods Enzymol. 100, 468-500; Kramer, W. et al. (1984) Nucleic Acids Res. 12, 9441-9456; Kramer, W. and Fritz, H. J. (1987) Methods Enzymol. 154, 350-367; and Kunkel, T. A. (1985) Proc. Natl. Acad. Sci. USA. 82, 488-492.) or the like. Alternatively, an amino acid mutation can occur in the natural world. It is generally preferred that an amino acid residue to be substituted should be substituted by another amino acid in which the side chain properties of the amino acid are conserved. Examples of the side chain properties of amino acids can include hydrophobic amino acids (A, I, L, M, F, P, W, Y, and V), hydrophilic amino acids (R, D, N, C, E, Q, G, H, K, S, and T), amino acids having an aliphatic side chain (G, A, V, L, I, and P), amino acids having a side chain containing a hydroxyl group (S, T, and Y), amino acids having a side chain containing a sulfur atom (C and M), amino acids having a side chain containing carboxylic acid or amide (D, N, E, and Q), amino acids having a side chain containing a base (R, K, and H), and amino acids having a side chain containing an aromatic group (H, F, Y, and W) (any character in parentheses denotes a single character code for the amino acid). It has already been known that a polypeptide having an amino acid sequence modified from a certain amino acid sequence by the deletion of one or several amino acid residues, the addition thereof, and/or the substitution thereof by other amino acids maintains the biological activity of the original polypeptide (Mark, D. F. et al., Proc. Natl. Acad. Sci. USA (1984) 81, 5662-5666; Zoller, M. J. & Smith, M. Nucleic Acids Research (1982) 10, 6487-6500; Wang, A. et al., Science 224, 1431-1433; and Dalbadie-McFarland, G. et al., Proc. Natl. Acad. Sci. USA (1982) 79, 6409-6413). Alternatively, sugar-chain modified EPO analogs such as NESP (Novel Erythropoietin Stimulating Protein; described in WO 85/02610, WO 91/05867, WO 95/05465, etc.), which is a sugar-chain modified EPO containing sialic acid attached to the N terminus of EPO, may be used.

Moreover, a fusion protein of EPO and a different protein may be used. To prepare such a fusion polypeptide, for example, DNA encoding EPO is ligated in frame to DNA encoding a different protein, and this ligation product may be introduced into an expression vector and allowed to be expressed as a fusion protein in a host. The different protein subjected to fusion with the EPO of the present invention is not particularly limited.

Moreover, chemically modified EPO may be used. Examples of the chemically modified EPO can include EPO bound with a compound such as an inorganic or organic compound, for example, polyethylene glycol or vitamin B12. Specific examples thereof can include polyethylene glycol-modified EPO described in Japanese Laid-open Patent publication No. 2001-64300.

The EPO-containing solution preparation of the present invention can be prepared, by adding a poloxamer, as an erythropoietin-containing solution preparation which is stable for long term even at a pH of approximately 7.0 and alleviates pain involved in injection. It was demonstrated, as shown later in Examples, that the EPO-containing solution preparation of the present invention containing a poloxamer added thereto and having a pH of approximately 7.0 reduces pain even without the addition of sugars such as mannitol.

A poloxamer is a non-ionic surfactant that is also used as an anti-adsorption agent for preventing a protein solution preparation from being adsorbed onto a container, and generally refers to a copolymer of ethylene oxide and propylene oxide. Specific examples thereof include a series of block copolymers of ethylene oxide and propylene oxide represented by the following general formula:

$$HO(C_2H_4O)_a(C_3H_6O)_b(C_2H_4O)_aH.$$

Poloxamers 124, 188, 237, 338, and 407 are listed as poloxamers in USP (US Pharmacopoeia). Poloxamer 188 described in USP is represented by the formula above wherein a and b represent 80 and 27, respectively, and has an average molecular weight of 7680 to 9510. Poloxamer 188 described in BP (British Pharmacopoeia) is represented by the formula above wherein a and b represent approximately 75 and approximately 30, respectively, and has an average molecular weight of 8350. EP (European Pharmacopoeia) further describes poloxamers 182, 184, and 331 in addition to those described above. Poloxamers 108, 335, 403, and the like can be used additionally. Moreover, Pluronic (trademark for BASF poloxamer) includes Pluronics L35, L43, L44, L61, L62, L64, F68, L81, P84, P85, F87, F88, L92, F98, L101, P103, P104, P105, F108, L121, P123, and F127. These Pluronics are also encompassed in the poloxamer of the present invention. Numbers represented by a and b in the structural formula above are generally a combination of 2 to 128 and 16 to 67, preferably a combination of 11 to 100 and 16 to 67, more preferably a combination of 50 to 100 and 20 to 40. Moreover, the average molecular weight is generally 1000 to 15000, preferably 2000 to 10000, more preferably 7000 to 10000.

It was demonstrated, as shown later in Examples, that any formulation obtained using a poloxamer-based surfactant more largely inhibits production of an EPO dimer after long-term storage and is more stable than formulations obtained using polyoxyethylene hydrogenated castor oil or polysorbate as a surfactant. A preferable poloxamer is poloxamer 108, 124, 188, 335, or 403, most preferably poloxamer 188.

The amount of the poloxamer added differs depending on the type of a poloxamer used and is generally 0.0001 to 10%, preferably 0.001 to 0.5%, more preferably 0.005 to 0.1%. Moreover, an EPO/poloxamer 188 ratio by weight is 0.001 to 5, preferably 0.017 to 1.2.

The EPO-containing solution preparation of the present invention can be prepared, by using a poloxamer as a surfactant, as an EPO-containing solution preparation which is stable even around pH 7.0, that is, has a high EPO residual rate even after long-term storage, inhibits production of a dimer or decomposition product, and alleviates pain.

The protein-containing preparation of the present invention may be supplemented with an amino acid as a stabilizer. The amino acid added as a stabilizer includes free amino acids and salts thereof such as sodium salts, potassium salts, and hydrochlorides. The amino acids can be added alone or in combination of two or more of them. The amino acid added as a stabilizer is not particularly limited. Examples of preferable amino acids can include leucine, tryptophan, serine, glutamic acid, arginine, histidine, and lysine. A preferable amino acid is histidine, arginine, or a salt thereof. Alternatively, the amino acid is preferably L-amino acid, most preferably L-histidine.

The amount of the amino acid added can be determined within a preferable range depending on the type of an amino acid used. The amount is generally 0.0001 to 5%. When arginine is used, the amount is preferably 0.01 to 4%, more preferably 0.1 to 1%. When histidine is used, the amount is preferably 0.05 to 1%, more preferably 0.05 to 0.5%, most preferably 0.05 to 0.2%.

The pH of the protein preparation of the present invention is 6.5 to 7.5, preferably 6.8 to 7.2, most preferably approximately 7.0.

Preferably, the EPO-containing solution preparation of the present invention is substantially free of a protein such as human serum albumin or purified gelatin as a stabilizer. Some protein preparations currently on the market contain a protein such as human serum albumin or purified gelatin added as a stabilizer for inhibiting the chemical or physical alteration of the protein. However, the addition of a protein as a stabilizer presents problems such as need of very complicated steps for removing viral contamination.

The amount of the EPO contained in the solution preparation of the present invention is generally 100 to 500000 IU/ml, preferably 200 to 200000 IU/ml, more preferably 750 to 108000 IU/ml, most preferably 1500 to 108000 IU/ml.

When the EPO solution preparation of the present invention has an EPO content of 48000 IU/mL, this EPO solution preparation after an accelerated test at 35° C. for 1 month has an EPO residual rate of 95% or more, preferably 97% or more, and has a dimer production rate of 1.0% or less, preferably 0.7% or less. Alternatively, this EPO solution preparation after an accelerated test at 35° C. for 3 months has an EPO residual rate of 93% or more, preferably 95% or more, and has a dimer production rate of 1.2% or less, preferably 1.0% or less.

The therapeutic agent of the present invention can be supplemented appropriately with, if necessary, suspending agents, solubilizers, stabilizers, tonicity agents, preservatives, anti-adsorption agents, diluents, excipients, pH adjusters, soothing agents, buffers, sulfur-containing reducing agents, antioxidants, and the like.

Examples of the suspending agents can include methyl cellulose, Polysorbate 80, hydroxyethyl cellulose, gum arabic, powdered tragacanth, carboxymethyl cellulose sodium, and polyoxyethylene sorbitan monolaurate.

Examples of the solubilizers can include polyoxyethylene hydrogenated castor oil, Polysorbate 80, nicotinic acid amide, polyoxyethylene sorbitan monolaurate, macrogol, and castor oil fatty acid ethyl ester.

Examples of the stabilizers can include dextran 40, methyl cellulose, gelatin, sodium sulfite, and sodium metasulfite.

Examples of the tonicity agents can include D-mannitol, sorbitol, and sodium chloride.

Examples of the preservatives can include methyl parahydroxybenzoate, ethyl parahydroxybenzoate, sorbic acid, phenol, cresol, and chlorocresol.

In addition to the poloxamer, for example, human serum albumin, lecithin, dextran, hydroxypropyl cellulose, methyl cellulose, polyoxyethylene hydrogenated castor oil, or polyethylene glycol may be added as an anti-adsorption agent.

Examples of the sulfur-containing reducing agents include those having a sulfhydryl group, such as N-acetylcysteine, N-acetylhomocysteine, thioctic acid, thiodiglycol, thioethanolamine, thioglycerol, thiosorbitol, thioglycolic acid and a salt thereof, sodium thiosulfate, glutathione, and thioalkanoic acid having 1 to 7 carbon atoms.

Examples of the antioxidants include erythorbic acid, dibutylhydroxytoluene, butylated hydroxyanisole, α-tocopherol, tocopherol acetate, L-ascorbic acid and a salt thereof, L-ascorbyl palmitate, L-ascorbyl stearate, sodium hydrogen sulfite, sodium sulfite, triamyl gallate, propyl gallate, and chelating agents such as disodium ethylenediaminetetraacetate (EDTA), sodium pyrophosphate, and sodium metaphosphate.

The solution preparation of the present invention may further contain usually-added ingredients including: inorganic salts such as sodium chloride, potassium chloride, calcium chloride, sodium phosphate, potassium phosphate, and sodium hydrogen carbonate; and organic salts such as sodium citrate, potassium citrate, and sodium acetate.

The EPO solution preparation of the present invention is prepared by dissolving these ingredients in an aqueous buffer solution known in the solution preparation field, such as a phosphate buffer solution (preferably, sodium monohydrogen phosphate-sodium dihydrogen phosphate-based) and/or a citrate buffer solution (preferably, a sodium citrate buffer solution).

The EPO solution preparation of the present invention is usually stored in, for example, a sealed and sterilized plastic or glass container. The container can be provided in a form having a prescribed dose, such as an ampoule, vial, or disposable syringe, or can also be provided in a form having a large dose, such as a bag or bottle for injection. The container can be conveniently provided in a form of a prefilled syringe.

The stabilized protein preparation of the present invention is usually administered through a parenteral administration route, for example, as an injection (e.g., subcutaneous, intravenous, or intramuscular injection) or transdermally, transmucosally, nasally, or transpulmonarily, or may be administered orally.

The present invention further provides a method for quantifying a protein in a trace amount, which is useful both for the quantification of the EPO-containing solution preparation of the present invention and for a purity test.

Heretofore, gel electrophoresis which is excellent in separation performance has often been used for determining the amounts of impurities in a protein solution. Gel electrophoresis has favorable detection sensitivity on the order of 0.6 to 1.2 ng/band in a silver staining method, a generally versatile high-sensitivity staining method, but has poor quantitative performance. Therefore, this technique is impossible to use in a quantitative method. On the other hand, methods relying on RI labeling and immunostaining after transfer to a membrane are used for achieving further improvement in sensitivity. The former has a risk of radioactive contamination and has poor general versatility. By contrast, the latter has sensitivity increased up to a pg order but produces variations due to complicated procedures. Therefore, this technique is unsuitable for quantification.

Thus, the present invention provides a generally versatile qualitative, quantitative, or purity test method for a protein in a trace amount having sensitivity equivalent to immunostaining.

The method for quantifying a protein in a trace amount according to the present invention includes the following steps:
binding a protein sample to a high-intensity fluorescent dye;
separating a desired analyte from the obtained sample by an appropriate separation means; and
quantifying the desired analyte and converting the amount of the analyte into the amount of the protein.

In the present invention, a fluorescent reagent is used for enhancing sensitivity. A fluorescent gel-staining reagent for fluorescently staining a gel after electrophoresis includes Ruby stain and SYPRO orange. These reagents are superior in quantitative performance to a silver staining method but inferior in detection sensitivity thereto. Moreover, these reagents perform staining after electrophoresis, as in silver staining, and therefore require complicated staining procedures. On the other hand, the fluorescent reagent Cyanine Dye used herein is unsuitable for staining after electrophoresis. However, this fluorescent reagent strongly forms a covalent bond with a protein via NHS (N-hydroxysuccinimide) or Maleimide and can therefore stain the protein before electrophoresis. Moreover, a site labeled by Cyanine Dye is a specific position ($NH_2$ group for NHS or SH group for Maleimide). Therefore, this dye produces few variations in the binding between Cyanine Dye and each protein, and achieves the securing of quantitative performance. Thus, the desired analyte in the separation step above is a conjugate of the protein and the fluorescent dye, including those bound via NHS, Maleimide, or the like.

In the method of the present invention, a method for binding a protein in a sample to a high-intensity fluorescent dye may usually be any method for chemically binding a fluorescent dye to an $NH_2$ or SH group in a general protein or may be performed by a method according to instructions for each commercially available high-intensity fluorescent dye. The reaction temperature thereof may usually fall within a range of 0° C. to 50° C. Specifically, the reaction temperature described in instructions for each commercially available high-intensity fluorescent dye may be used. For carrying out quantitative measurement of a sample as in the present invention, it may be performed under low-temperature conditions without freezing the sample, preferably at 0° C. to 10° C., more preferably 0° C. to 5° C., most preferably approximately 1° C., for uniformly staining proteins in the sample.

Furthermore, the use of Cyanine Dye permits detection as sensitive as dozens of pg/band, which is equivalent or superior to that of immunostaining. This allows Cyanine Dye to be used in a qualitative test. Furthermore, the use of this fluorescent dye in combination with a calibration curve of a standard or an internal standard substance also permits the quantification of a solution of a protein in a trace amount. Moreover, the method using Cyanine Dye serves as a purity test having a quantification range of a $10^4$ order or more (dozens of pg to around 100 ng/band) without the use of a standard or the like and permits an accurate evaluation of the content of impurities such as aggregates at 0.1% or less.

In addition, staining before electrophoresis can reduce the amount of reagents used. Therefore, Cyanine Dye is also superior in cost to a fluorescent reagent used in staining after electrophoresis.

The high-intensity fluorescent dye of the present invention may be any fluorescent dye that strongly forms a covalent bond with a protein either directly or via NHS, Maleimide, or the like and has a wide quantification range (dynamic range) of $10^4$ or more. For example, a Cyanine Dye-based dye such as Cy3, Cy3.5, Cy5, and Cy5.5 Mono-reactive Dyes (NHS-type and Maleimide-type) (manufactured by GE Healthcare) can be used. An NHS-type Cy3 Mono-reactive Dye is preferable.

Moreover, for example, protein labeling kits of a Sulfonated Coumarin or Sulfonated rhodamine Dye such as Alexa Fluor 350, 405, 430, 488, 532, 546, 555, 568, 594, 633, 647, 680, 700, and 750 (manufactured by Molecular Probes) and protein labeling kits of HiLyte Fluor 555, 647, and the like (manufactured by DOJINDO) can also be used as additional high-sensitivity fluorescent dyes of the present invention.

In the method of the present invention, a means for appropriately separating a desired analyte from the sample is any of general electrophoresis methods such as SDS-PAGE, capillary electrophoresis, and microchip electrophoresis. Alternatively, the desired analyte may be separated by HPLC-based gel filtration chromatography, ion-exchange chromatography, reverse-phase chromatography, or the like. A separation means using electrophoresis or HPLC is preferable.

The separation using electrophoresis adopts staining before electrophoresis and therefore requires no gel staining procedures after electrophoresis for capturing migrating images. The use of a gel immobilized on glass achieves the capture of migrating images by use of a fluorescent gel imager immediately after the washing of the glass plate surface with water after the completion of electrophoresis.

Moreover, the high-intensity fluorescent dye of the present invention can achieve staining before measurement and can therefore be applied to not only electrophoresis but also other separation means such as HPLC fluorescence detectors.

The use of the quantitative method of the present invention achieves sensitive quantification of EPO in the EPO-containing solution preparation. Furthermore, the quantitative method of the present invention can also be used in the quantification of a protein other than EPO. As shown later in Examples, the quantitative method of the present invention produces favorable calibration curves at varying protein concentrations in the quantification of an antibody protein hPM-1, which is a humanized anti-IL-6 receptor antibody, or BSA (bovine serum albumin), and achieved very highly sensitive detection under all the conditions tested. Thus, the method of the present invention is remarkably excellent as a method for quantifying a solution containing a protein in a trace amount and has a wide range of application.

The present invention will be described further specifically with reference to Examples below. However, the scope of the present invention is not intended to be limited to them. One skilled in the art can make various changes or modifications on the basis of the description of the present invention, and these changes or modifications are also incorporated in the present invention.

An EPO sample used in Examples below was genetically recombinant EPO (manufactured by Chugai Pharmaceutical Co., Ltd.) obtained using CHO cells.

EXAMPLES

Example 1

Pain Comparison Test on Formulations

A preparation of a formulation 1 or 2 shown in Table 1 below was injected subcutaneously to either arm of the same test subjects in a double-blind manner. The test subjects themselves evaluated pain involved in injection. The obtained results are shown in Table 2.

TABLE 1

| Component | Formulation 1 | Formulation 2 |
|---|---|---|
| EPO conc. (IU/ml) | 12000 | 12000 |
| Buffer | Phosphate | Phosphate |
| conc. (mmol/l) | 10 | 2 |
| Surfactant | Polysorbate 80 | Poloxamer 188 |
| conc. (%) | 0.005 | 0.05 |
| Stabilizer | L-Histidine | L-Histidine |
| conc. (%) | 0.1 | 0.1 |
| The others | Sodium Chloride | Sodium Chloride |
| conc. (mmol/l) | 135 | 143 |
| pH | 6.0 | 7.0 |
| Osmolarity | 1.0 | 1.0 |

TABLE 2

Comparison of the injection pain between 2 formulations (continuously-administered) Frequency table and signed rank test

| | Judgment | | | | | | |
|---|---|---|---|---|---|---|---|
| | 1 | 2 | 3 | 4 | 5 | Total | Signed rank test |
| Formulation1/ Formulation2 | 13 (72.2) | 5 (27.8) | 0 (0.0) | 0 (0.0) | 0 (0.0) | 18 (100.0) | S = −85.500 $P < 0.001$ |

Upper Head-count
Lower Appearance ratio (%)
Judgment
1. Formulation 1 causes the pain more than Formulation 2
2. Formulation 1 causes the pain slightly more than Formulation 2
3. Formulation 1 and Formulation 2 cause the pain of the same strength
4. Formulation 2 causes the pain slightly more than Formulation 1
5. Formulation 2 causes the pain more than Formulation 1

In the evaluation of pain by comparison among the test subjects, 100% of the test subjects concluded that Formulation 1 causes stronger pain than that caused by Formulation 2, demonstrating that Formulation 2 is significantly painless.

Example 2

Stability Test on Formulations

Two formulations shown below were subjected to a severe test at 35° C. for comparing stability.

These formulations were sterile-filtered after preparation and charged into sterilized syringes, which were then capped. The formulations used in the test and the test results are shown in Table 3.

TABLE 3

| | Component | Formulation 3 | Formulation 4 |
|---|---|---|---|
| | EPO conc. (IU/ml) | 48000 | 48000 |
| | Buffer | Phosphate | Phosphate |
| | conc. (mmol/l) | 6.7 | 25 |
| | Surfactant | Polysorbate 80 | Poloxamer 188 |
| | conc (%) | 0.005 | 0.05 |
| | Stabilizer | L-Histidine | L-Histidine |
| | Conc (%) | 0.1 | 0.1 |
| | The others | Mannitol | Sodium Chloride |
| | conc. | 1.8% | 120 mmol/l |
| | pH | 6.9 | 6.9 |
| | Osmolarity | 1.0 | 1.0 |
| Initial | EPO conc. (IU/ml) | 48845 | 47985 |
| | Dimer (%) | 0.3 | 0.3 |
| | Decomposition product (%) | <0.5 | <0.5 |

TABLE 3-continued

|  | Component | Formulation 3 | Formulation 4 |
|---|---|---|---|
| 35° C.-1 month | Residual ratio (%) | 96.4 | 98.4 |
|  | Dimer (%) | 1.3 | 0.4 |
|  | Decomposition product (%) | <0.5 | <0.5 |
| 35° C.-3 months | Residual ratio (%) | 94.6 | 95.5 |
|  | Dimer (%) | 3.2 | 0.9 |
|  | Decomposition product (%) | 1.0 | 0.6 |

Formulation 4 has a higher EPO residual rate than that of Formulation 3 and significantly inhibits production of a dimer or decomposition product, demonstrating that Formulation 4 is stable.

The following test methods were used in the test above.

(1) Measurement of Residual Rate

The amount of EPO was measured by liquid chromatography to determine its residual rate with respect to the initial product.

Column used: 214TP54 (Size: 250 mm×4.6 mm I.D., particle size: 5 μm); manufactured by Vydac Mobile Phase A: water:acetonitrile:TFA=400:100:1

B: water:acetonitrile:TFA=100:400:1

A:B=65:35→A:B=0:100 performed using a linear gradient (2) Measurement of Dimer

DMSO containing a fluorescent reagent (NHS-type Cy3 Mono-reactive Dye) dissolved therein was added to a sample having an EPO concentration diluted to 1250 IU to label the EPO. Then, a sample buffer containing SDS was added thereto, and the mixture was heated at 50° C. for 15 minutes. A 15 μL aliquot thereof was tested by electrophoresis. The gel after electrophoresis was read in an image analyzer to calculate the peak area % of a dimer.

Gel used: 12.5% tris-glycine gel (3) Measurement of Low-Molecular-Weight Decomposition Product A sample buffer containing SDS and mercaptoethanol was added to a sample having an EPO concentration diluted to 3000 IU, and the mixture was heated at 50° C. for 15 minutes. A 7.5 μL aliquot thereof was tested by electrophoresis. After detection by western blotting using an anti-EPO antibody, the amount of a low-molecular-weight decomposition product in the sample was calculated from the calibration curve of a 25 to 500 ng/mL purified product of the decomposition product.

Gel used: 8 to 16% tris-glycine gel

Example 3

Influence of Surfactant Species

To confirm the influence of a surfactant on EPO stability, stability was confirmed using the formulations below.

These formulations were sterile-filtered after preparation and charged into washed and sterilized vials, which were then capped. A test method thereof was conducted according to the method for measurement of a dimer of Example 2. The formulations used in the test and the test results are shown in Table 4.

TABLE 4

|  |  | Formulation | | | | |
|---|---|---|---|---|---|---|
|  |  | 5 | 6 | 7 | 8 | 9 |
| EPO conc. (IU/mL) | | 48000 | 48000 | 48000 | 48000 | 48000 |
| Buffer | | Phos. | Phos. | Phos. | Phos. | Phos. |
| conc. (mmol/l) | | 25 | 25 | 25 | 25 | 25 |
| Surfactant | | HCO-40 | HCO-60 | HCO-80 | PS80 | PS20 |
| conc. (%) | | 0.0425 | 0.0645 | 0.0845 | 0.005 | 0.0043 |
| Stabilizer | | L-His | L-His | L-His | L-His | L-His |
| conc. (%) | | 1.0 | 1.0 | 1.0 | 1.0 | 1.0 |
| pH | | 7.0 | 7.0 | 7.0 | 7.0 | 7.0 |
| Dimer | Initial | 0.2 | 0.2 | 0.3 | 0.2 | 0.1 |
| (%) | 35° C.-1 month | 0.8 | 0.6 | 0.6 | 1.0 | 0.9 |
|  | 35° C.-3 months | 2.0 | 2.1 | 2.2 | 3.2 | 2.9 |

|  | Formulation | | | | |
|---|---|---|---|---|---|
|  | 10 | 11 | 12 | 13 | 14 |
| EPO conc. (IU/mL) | 48000 | 48000 | 48000 | 48000 | 48000 |
| Buffer | Phos. | Phos. | Phos. | Phos. | Phos. |
| conc. (mmol/l) | 25 | 25 | 25 | 25 | 25 |
| Surfactant | PX403 | PX124 | PX335 | PX108 | PX188 |
| conc. (%) | 0.022 | 0.0084 | 0.025 | 0.0185 | 0.033 |
| Stabilizer | L-His | L-His | L-His | L-His | L-His |
| conc. (%) | 1.0 | 1.0 | 1.0 | 1.0 | 1.0 |
| pH | 7.0 | 7.0 | 7.0 | 7.0 | 7.0 |

TABLE 4-continued

| | | | | | | |
|---|---|---|---|---|---|---|
| Dimer (%) | Initial | 0.1 | 0.2 | 0.1 | 0.1 | 0.1 |
| | 35° C.-1 month | 0.5 | 0.5 | 0.4 | 0.4 | 0.5 |
| | 35° C.-3 months | 1.0 | 0.8 | 1.1 | 1.0 | 1.0 |

HCO: Hydrogenated Castor Oil
PS: Polysorbate
PX: Poloxamer

Formulations 10 to 14 obtained using a poloxamer as a surfactant produced more significantly reduced amounts of a dimer in an accelerated test at 35° C. for 3 months and were more stable than formulations obtained using polyoxyethylene hydrogenated castor oil or polysorbate as a surfactant. Moreover, all the poloxamer-based surfactants inhibited the production of an EPO dimer.

Example 4

Influence of EPO Content on Stability

Formulations having a pH of 7.0 and containing poloxamer 188 added as a surfactant were subjected to a stability test for confirming the influence of EPO content on stability.

These formulations were sterile-filtered after preparation and charged into sterilized syringes, which were then capped. A test method thereof was conducted according to the measurement method of Example 2. The formulations used in the test and the test results are shown in Table 5.

Example 5

Discussion of EPO Purity Test Method Using Cyanine Dye (Cy3)

Preparation of EPO solution: A dilution buffer solution (0.1 M phosphate buffer solution (pH 7.4) containing 0.005% Polysorbate 80) was added to an EPO standard (EPO concentration: 1 mg/mL) to prepare an EPO solution having each content.

(1) Confirmation of Detection Limit

Figure 1:
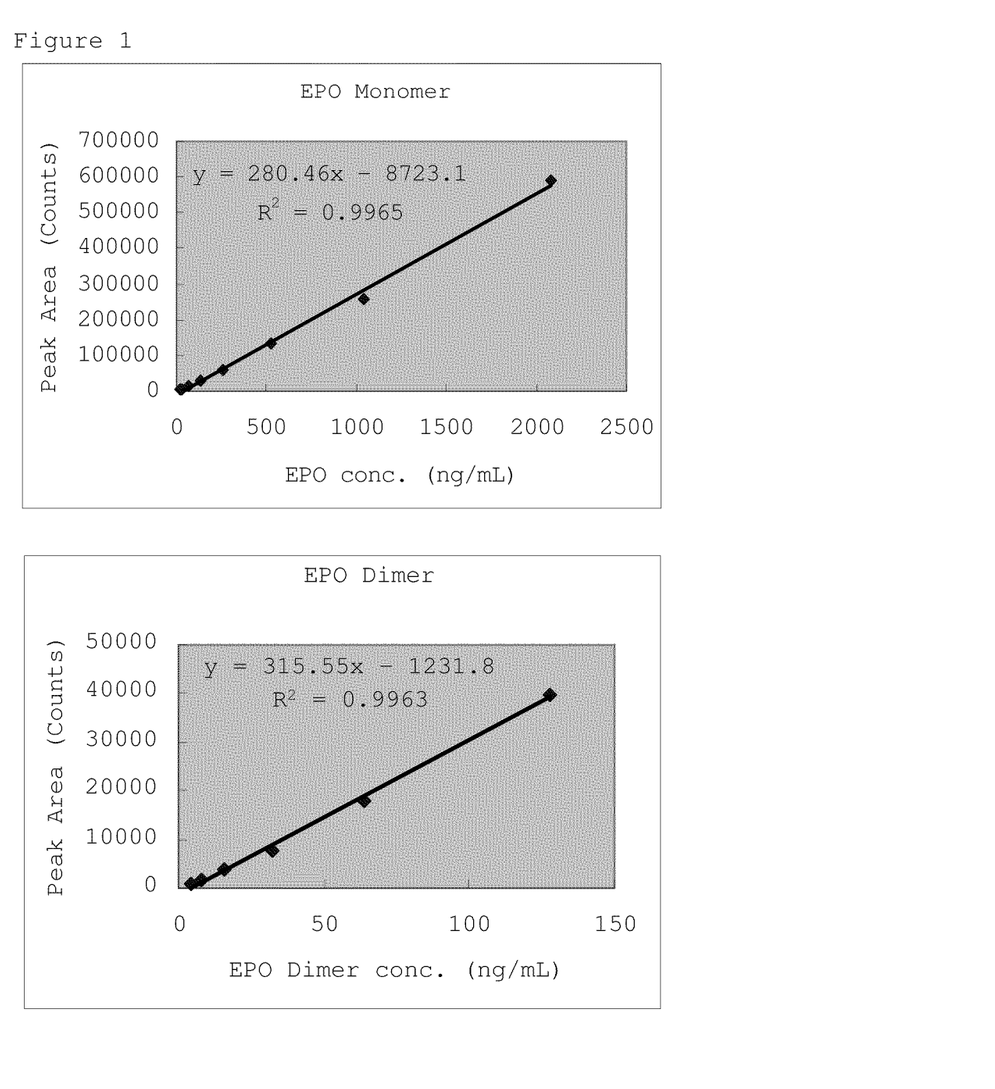
FIG. 1 is a diagram showing results of confirming detection limits by measuring EPO and an EPO dimer at varying concentrations and preparing calibration curves.

2 µL of a Cy3 stock solution (1 vial of NHS-type Cy3 Mono-reactive Dye dissolved in 100 µL of DMSO) was added to 60 µL of each solution having an EPO concentration of 16.3 ng/mL to 2083.3 ng/mL or an EPO dimer concentration of 2 ng/mL to 128 ng/mL, followed by reaction at approximately 1° C. for 4 hours. After the completion of reaction, 24 µL of a sample buffer containing SDS was added thereto, and the mixture was heated at 50° C. for 15 minutes. Then, a 15 µL

TABLE 5

| | Component | Formulation 15 | Formulation 16 | Formulation 17 | Formulation 18 | Formulation 19 |
|---|---|---|---|---|---|---|
| | EPO conc. (IU/ml) | 1500 | 12000 | 48000 | 72000 | 108000 |
| | Buffer | Phosphate | Phosphate | Phosphate | Phosphate | Phosphate |
| | Surfactant | Poloxamer 188 | Poloxamer 188 | Poloxamer 188 | Poloxamer 188 | Poloxamer 188 |
| | Conc. (%) | 0.05 | 0.05 | 0.05 | 0.05 | 0.05 |
| | Stabilizer | L-His | L-His | L-His | L-His | L-His |
| | Conc.(%) | 0.1 | 0.1 | 0.1 | 0.1 | 0.1 |
| | The others conc.(mmol/l) | Sodium Chloride 143 | Sodium Chloride 143 | Sodium Chloride 137 | Sodium Chloride 133 | Sodium Chloride 173 |
| | pH | 7.0 | 7.0 | 7.0 | 7.0 | 7.0 |
| Initial | EPO conc. (IU/ml) | 1565 | 11883 | 46637 | 70434 | 105681 |
| | Dimer (%) | 0.3 | 0.5 | 0.3 | 0.3 | 0.4 |
| | Decomposition product (%) | <1.0 | <0.5 | <0.5 | <0.5 | <0.5 |
| 10° C.-6 months | Residual ratio (%) | 97.5 | 97.9 | 98.8 | 99.7 | 99.6 |
| | Dimer (%) | 0.1 | 0.1 | 0.2 | 0.2 | 0.1 |
| | Decomposition product (%) | <1.0 | <0.5 | <0.5 | <0.5 | <0.5 |
| 10° C.-12 months | Residual ratio (%) | 95.3 | 100.6 | 101.3 | 101.8 | 101.7 |
| | Dimer (%) | 0.2 | 0.2 | 0.2 | 0.2 | 0.2 |
| | Decomposition product (%) | <1.0 | <0.5 | <0.5 | <0.5 | <0.5 |

It could be confirmed that the formulations having an EPO content of 1500 to 108000 IU/mL are stable at least at 10° C. for 1 year. It could further be confirmed in this Example that an EPO/poloxamer 188 ratio even in a range of 0.017 to 1.2 has no stability problem.

*EPO 180000 IU=1 mg aliquot thereof was subjected to electrophoresis. The gel was read in a fluorescent image analyzer. Calibration curves were prepared to confirm detection limits. The obtained results are shown in FIG. 1.

A favorable calibration curve ($R^2$=0.9965) was obtained in the solutions having an EPO concentration of 16.3 ng/mL to 2083.3 ng/mL (174 pg to 22.3 ng in terms of 1 well). Moreover, a peak could not be detected in the solution having an EPO dimer concentration of 2 ng/mL. However, a favorable calibration curve ($R^2$=0.9963) was obtained in the solutions having an EPO dimer concentration of 4 ng/mL to 128 ng/mL (43 pg to 1.37 ng in terms of 1 well). Detection with sensitivity as very high as 43 pg/well was achieved.

(2) Confirmation of Precision

An EPO dimer was added to an EPO solution having a concentration of 1250 IU/mL to prepare a solution containing 0.094 to 2.256% EPO dimer with respect to EPO. For this solution, precision was confirmed (n=4). The obtained results are shown in Table 6.

TABLE 6

|  | 2.256% | 1.880% | 1.504% | 1.128% | 0.940% | 0.752% | 0.376% | 0.188% | 0.094% |
|---|---|---|---|---|---|---|---|---|---|
| n = 1 | 2.243 | 1.773 | 1.358 | 1.099 | 1.009 | 0.65 | 0.31 | 0.153 | 0.101 |
| n = 2 | 2.102 | 1.901 | 1.452 | 0.999 | 0.799 | 0.68 | 0.312 | 0.14 | 0.068 |
| n = 3 | 2.198 | 1.822 | 1.432 | 0.976 | 0.791 | 0.72 | 0.314 | 0.12 | 0.058 |
| n = 4 | 2.145 | 1.819 | 1.359 | 0.956 | 0.904 | 0.725 | 0.406 | 0.188 | 0.138 |
| Average | 2.172 | 1.829 | 1.400 | 1.008 | 0.876 | 0.694 | 0.336 | 0.150 | 0.091 |
| S.D. | 0.0615 | 0.0531 | 0.0489 | 0.0635 | 0.1027 | 0.0354 | 0.0470 | 0.0286 | 0.0363 |
| % CV | 2.831 | 2.905 | 3.492 | 6.301 | 11.724 | 5.109 | 14.017 | 19.031 | 39.797 |

C.V. (coefficient of variation) was approximately 40% at the EPO dimer concentration of 0.094% and was 20% or less at the EPO dimer concentration of 0.188% or more, demonstrating favorable precision.

Example 6

Discussion of Antibody (hPM-1) Purity Test Method Using Cyanine Dye (Cy3)

Figure 2:
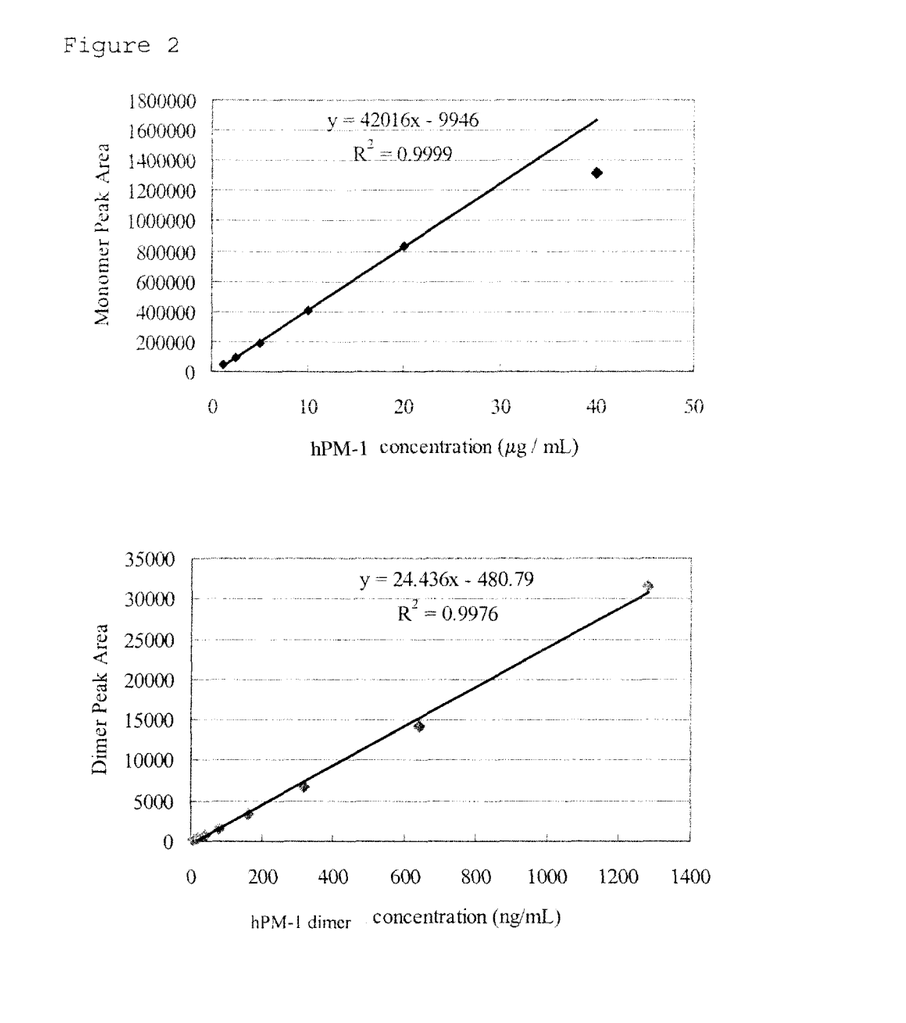
FIG. 2 is a diagram showing results of confirming detection limits by measuring hPM-1 and an hPM-1 dimer at varying concentrations and preparing calibration curves.

An antibody protein hPM-1 used in the tests below was a humanized anti-IL-6 receptor antibody (see WO 92-19759).
(1) Confirmation of Detection Limit 2 μL of a Cy3 stock solution (1 vial of NHS-type Cy3 Mono-reactive Dye dissolved in 100 μL of DMSO) was added to 60 μL of each solution having an hPM-1 concentration of 1.25 μg/mL to 40 μg/mL or an hPM-1 dimer concentration of 2.5 ng/mL to 1280 ng/mL, followed by reaction at approximately 1° C. for 4 hours. After the completion of reaction, 24 μL of a sample buffer containing SDS was added thereto, and the mixture was heated at 50° C. for 15 minutes. Then, a 15 μL aliquot thereof was subjected to electrophoresis. The gel was read in a fluorescent image analyzer. Calibration curves were prepared to confirm detection limits. The obtained results are shown in FIG. 2.

A favorable calibration curve ($R^2$=0.9999) was obtained for the solutions having an hPM-1 concentration of 1.25 μg/mL to 20 μg/mL (13.4 ng to 214 ng in terms of 1 well). Moreover, a peak could not be detected for the solution having an hPM-1 dimer concentration of 5 ng/mL. However, a favorable calibration curve ($R^2$=0.9976) was obtained for the solutions having an hPM-1 dimer concentration of 10 ng/mL to 1280 ng/mL (107 pg to 13.7 ng in terms of 1 well). Detection with sensitivity as very high as 107 pg/well was achieved.
(2) Confirmation of Precision A solution having an hPM-1 concentration of 10 μg/mL and a dimer content of 0.05 to 6.4% was prepared. For this solution, precision was confirmed. The obtained results are shown in Table 7.

TABLE 7

|  | Expected ratio (%) | | | | | | | |
|---|---|---|---|---|---|---|---|---|
|  | 6.4 | 3.2 | 1.6 | 0.8 | 0.4 | 0.2 | 0.1 | 0.05 |
| gel_#1 | 6.260 | 3.254 | 1.691 | 0.948 | 0.559 | 0.417 | 0.283 | 0.248 |
| gel_#2 | 6.329 | 3.266 | 1.735 | 0.981 | 0.569 | 0.427 | 0.301 | 0.261 |
| gel_#3 | 6.275 | 3.197 | 1.732 | 0.983 | 0.536 | 0.375 | 0.302 | 0.238 |
| Average | 6.288 | 3.239 | 1.719 | 0.971 | 0.555 | 0.406 | 0.295 | 0.249 |
| S.D. | 0.036 | 0.037 | 0.025 | 0.020 | 0.017 | 0.028 | 0.011 | 0.012 |
| R.S.D. (%) | 0.577 | 1.138 | 1.430 | 2.025 | 3.051 | 6.791 | 3.621 | 4.632 |

C.V. (%) was up to approximately 7%, demonstrating favorable precision.

Example 7

Discussion of EPO and BSA Purity Test Methods Using Cyanine Dye (Cy5), Alexa 647, and HiLyte Fluor 647

(1) Confirmation of Detection Limit 3.3 μL of a Cy5 stock solution (1 vial of NHS-type Cy5 Mono-reactive Dye dissolved in 100 μL of DMSO), 1 μL of an Alexa 647 stock solution (1 vial of NHS-type Alexa 647 dissolved in 10 μL of DMSO), or 1 μL of a HiLyte Fluor 647 stock solution (1 vial of NHS-type HiLyte Fluor 647 dissolved in 10 μL of DMSO) was added to 100 μL of a solution of 10 μg/mL EPO or BSA (prepared with 0.1 M NaHCO$_3$), followed by reaction at approximately 1° C. for 18 hours. After the completion of reaction, each reaction solution was diluted with a dilution buffer solution (0.1 M phosphate buffer solution (pH 7.4) containing 0.005% Polysorbate 80) at a common ratio of 3 to six concentrations from 0.046 ng/mL to 11.1 ng/mL (corresponding to 0.34 pg/well to 83 pg/well). After dilution, 20 μL of a sample buffer containing SDS was added to a 40 μL aliquot of each solution, and the mixture was heated at 50° C. for 15 minutes. Then, a 10 μL aliquot thereof was subjected to electrophoresis. The gel was read in a fluorescent image analyzer. Calibration curves were prepared to confirm detection limits. The results obtained for EPO and for BSA are shown in FIGS. 3 and 4, respectively.

Figure 3:
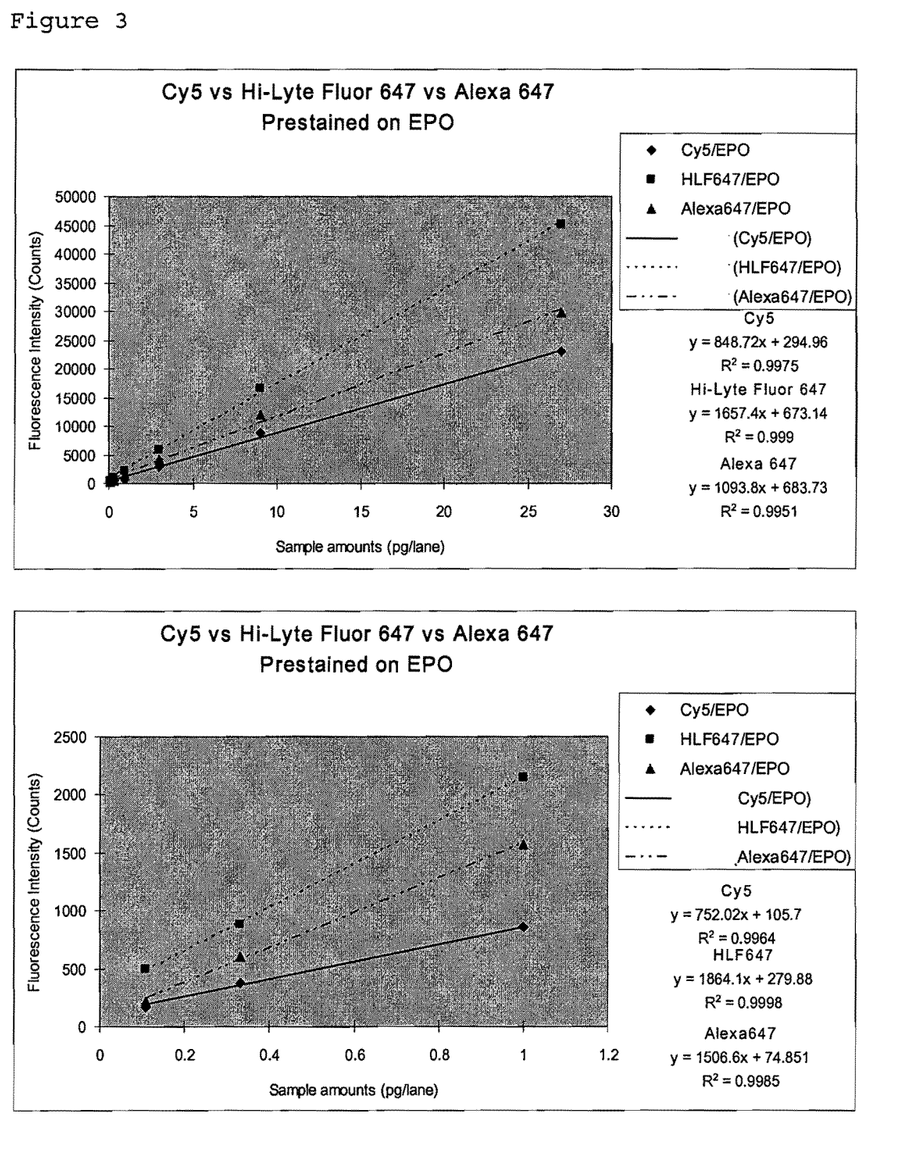
FIG. 3 is a graph showing results of a purity test method wherein EPO was measured using fluorescent dyes Cy5, Alexa 647, and HiLyte Fluor 647.
Figure 4:
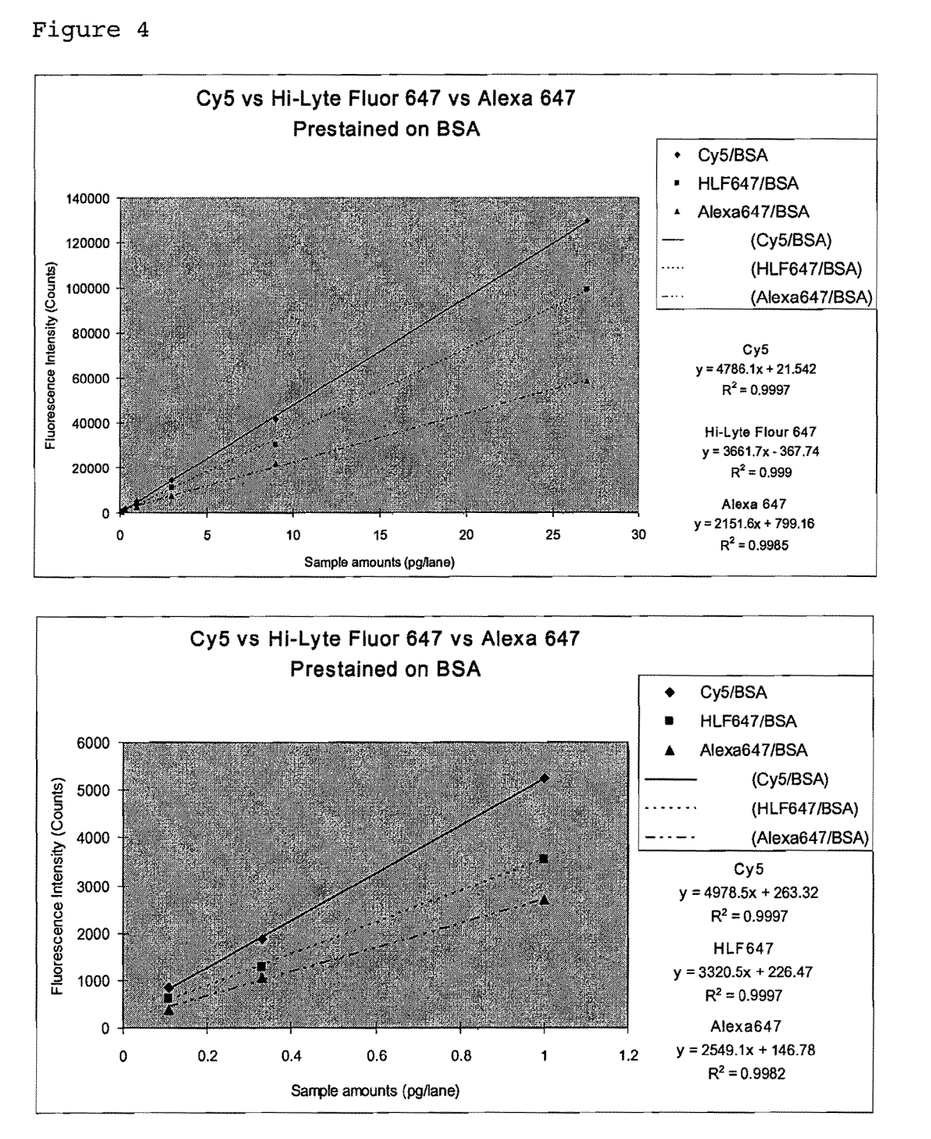
FIG. 4 is a graph showing results of a purity test method wherein BSA was measured using fluorescent dyes Cy5, Alexa 647, and HiLyte Fluor 647.

As is evident from FIGS. 3 and 4, a favorable calibration curve was obtained for both the solutions having EPO or BSA concentrations of 0.046 ng/mL to 11.1 ng/mL (0.34 pg/well to 83 pg/well in terms of 1 well). Detection with sensitivity as very high as 0.34 pg/well was achieved under all the conditions.

Example 8

Discussion of Enhancement in Sensitivity of Microchip Electrophoresis System Using Prestaining (1) Confirmation of Detection Limit 3.3 μL of a Cy5 stock solution (1 vial of NHS-type Cy5 Mono-reactive Dye dissolved in 100 μL of DMSO), 1 μL of an Alexa 647 stock solution (1 vial of NHS-type Alexa 647 dissolved in 10 μL of DMSO), or 1 μL of a HiLyte Fluor 647 stock solution (1 vial of NHS-type HiLyte Fluor 647 dissolved in 10 μL of DMSO) was added to 100 μL of a solution of 1 mg/mL BSA (prepared with 0.1 M $NaHCO_3$), followed by reaction at approximately 1° C. for 18 hours. After the completion of reaction, each reaction solution was diluted with a dilution buffer solution (0.1 M phosphate buffer solution (pH 7.4) containing 0.005% Polysorbate 80) at a common ratio of 2 to ten concentrations from 0.046 ng/mL to 50 ng/mL. After dilution, measurement was performed according to the protocol of a microchip electrophoresis system, and calibration curves were prepared from the values obtained by the system to confirm detection limits. The results obtained using Cy5, Alexa 647, and HiLyte Fluor 647 are shown in FIGS. 5, 6, and 7, respectively.

Figure 5:
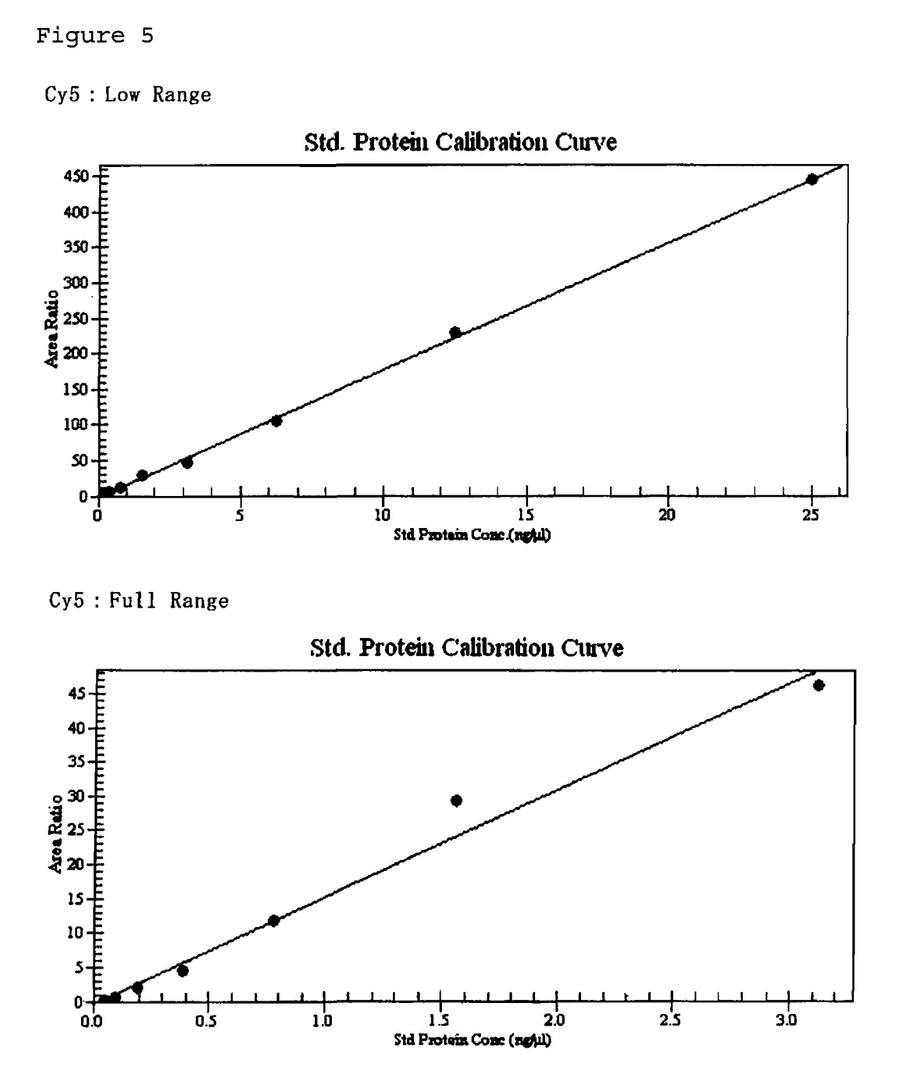
FIG. 5 is a graph showing results of a purity test method wherein BSA was measured with a microchip electrophoresis system using a fluorescent dye Cy5.
Figure 6:
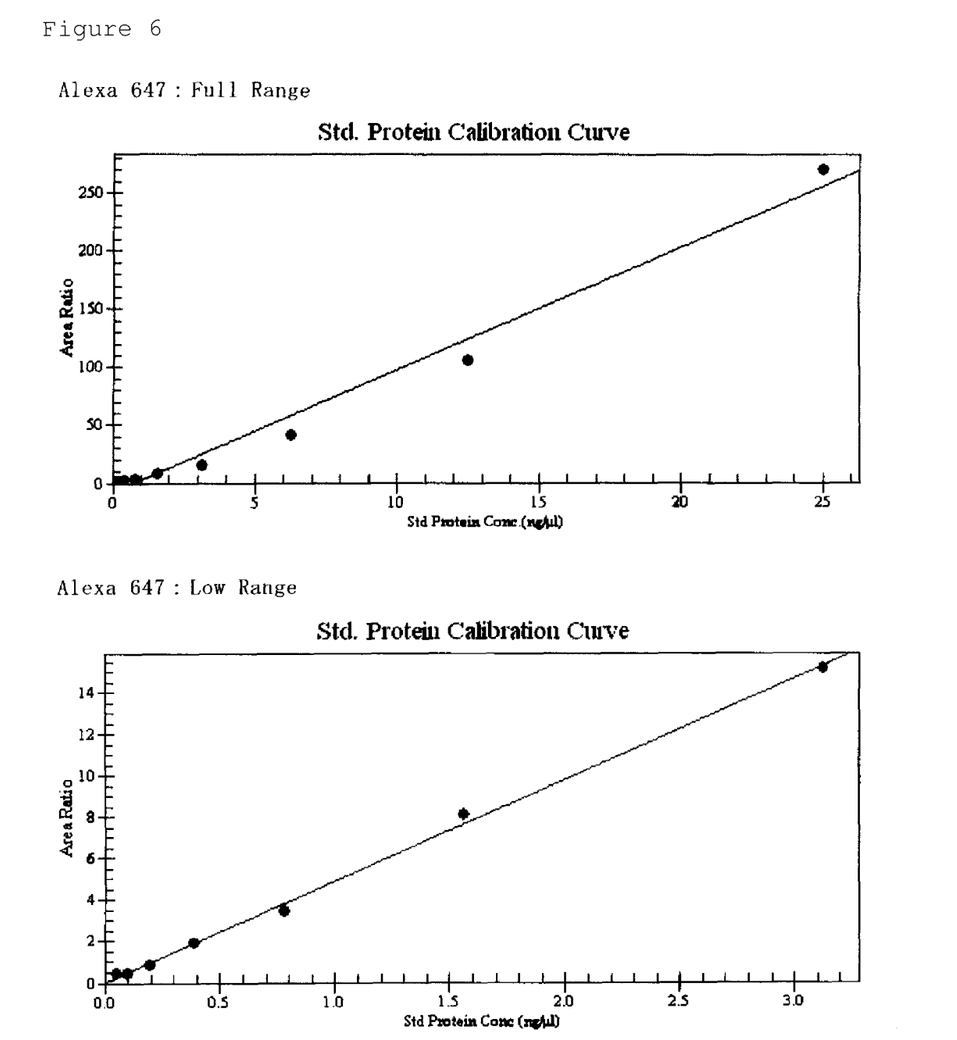
FIG. 6 is a graph showing results of a purity test method wherein BSA was measured with a microchip electrophoresis system using a fluorescent dye Alexa 647.
Figure 7:
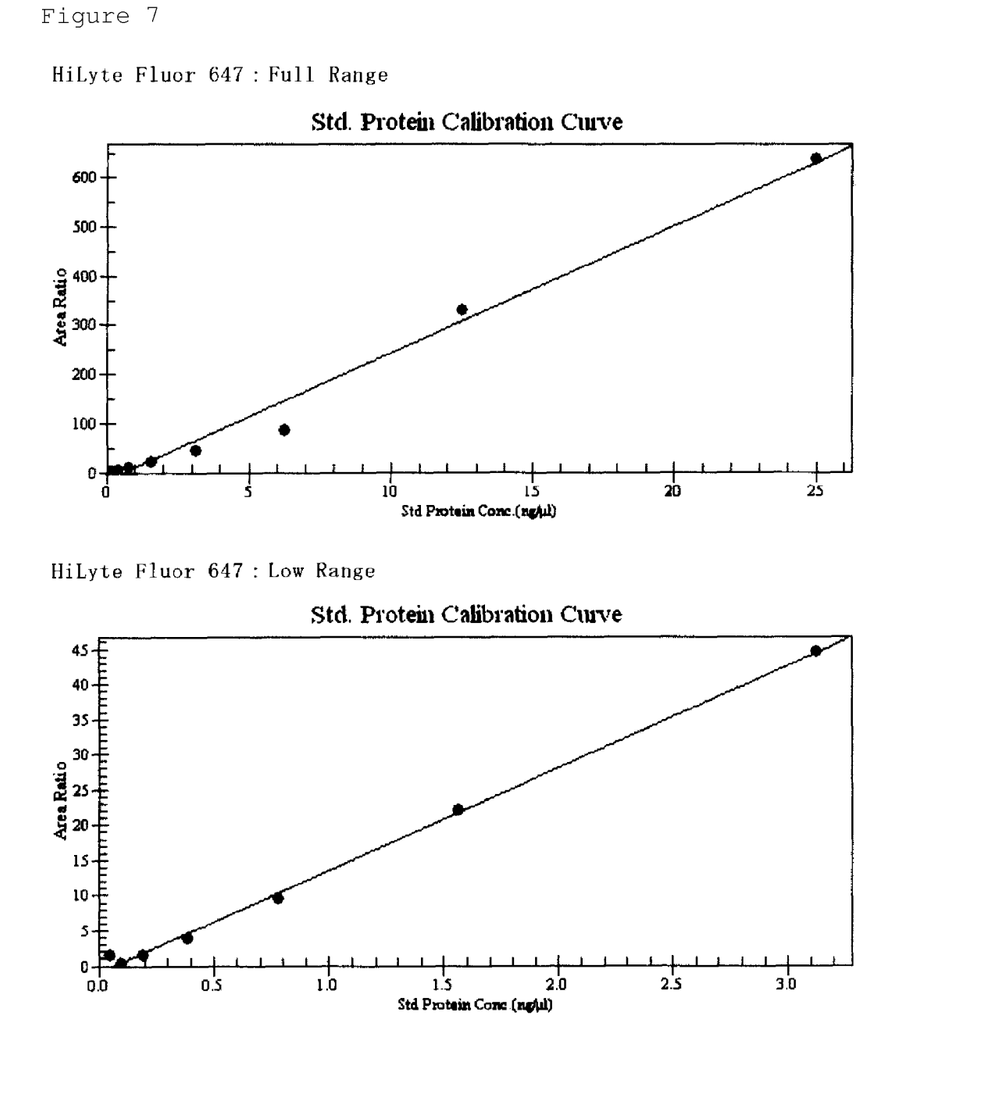
FIG. 7 is a graph showing results of a purity test method wherein BSA was measured with a microchip electrophoresis system using a fluorescent dye HiLyte Fluor 647.

As is evident from FIGS. 5 to 7, a favorable calibration curve was obtained using all these types of fluorescent dyes. Sensitivity enhancement that is 250 times or more compared to the results of measuring BSA in the same way according to the measurement method using the microchip electrophoresis system used in this discussion could be accomplished.

The invention claimed is:

1. A solution preparation comprising erythropoietin, a poloxamer, and having a pH of 6.5 to 7.5, and further comprising an amino acid or a salt thereof as a stabilizer, wherein the amino acid is selected from tryptophan, serine, arginine, histidine, lysine and mixtures thereof.

2. The preparation according to claim 1, wherein the poloxamer is poloxamer 188.

3. The preparation according to claim 1, wherein the amino acid is histidine or arginine.

4. The preparation according to claim 1, wherein the pH is 6.8 to 7.2.

5. The preparation according to claim 1, wherein the preparation is free of a protein as a stabilizer.

6. The preparation according to claim 1, wherein the preparation is free of a sugar as a stabilizer.

7. A solution preparation comprising erythropoietin, a poloxamer, and L-histidine as a stabilizer, and having a pH of 6.8 to 7.2.

8. The preparation according to claim 7, wherein the preparation is free of a protein as a stabilizer.

9. The preparation according to claim 7, wherein the preparation is free of a sugar as a stabilizer.

10. A method for inhibiting production of an erythropoietin dimer after long-term storage of a solution preparation comprising erythropoietin, the method comprising the steps
    (i) maintaining a pH of 6.5 to 7.5 in the solution;
    (ii) adding a poloxamer; and
    (iii) adding an amino acid or a salt thereof as a stabilizer, wherein the amino acid is selected from tryptophan, serine, arginine, histidine, lysine and mixtures thereof
wherein the steps (i) to (iii) are performed during or immediately after the preparation of the erythropoietin solution.

11. A method for stabilizing a solution preparation comprising erythropoietin by adding a poloxamer, and an amino acid or a salt thereof during or immediately after preparation of the erythropoietin solution, wherein the solution preparation has a pH of 6.5 to 7.5 and the amino acid is selected from tryptophan, serine, arginine, histidine, lysine and mixtures thereof.

* * * * *

UNITED STATES PATENT AND TRADEMARK OFFICE
CERTIFICATE OF CORRECTION

PATENT NO. : 8,546,329 B2
APPLICATION NO. : 12/293493
DATED : October 1, 2013
INVENTOR(S) : Mizushima et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 723 days.

Signed and Sealed this

Fifteenth Day of September, 2015

Michelle K. Lee
*Director of the United States Patent and Trademark Office*